US00PP34306P2

(12) United States Plant Patent
Horvath

(10) Patent No.: US PP34,306 P2
(45) Date of Patent: Jun. 7, 2022

(54) ***ALLIUM HYBRID* PLANT NAMED 'BIG BEAUTY'**

(50) Latin Name: ***Allium* hybrid**
Varietal Denomination: Big Beauty

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 17/300,823

(22) Filed: Nov. 22, 2021

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Annette H Para

(57) ABSTRACT

A new, distinct *Allium* hybrid plant as shown and described, characterized by gray green foliage in combination with light purple to pink flowers, on 60 cm stems.

1 Drawing Sheet

Figure 1:
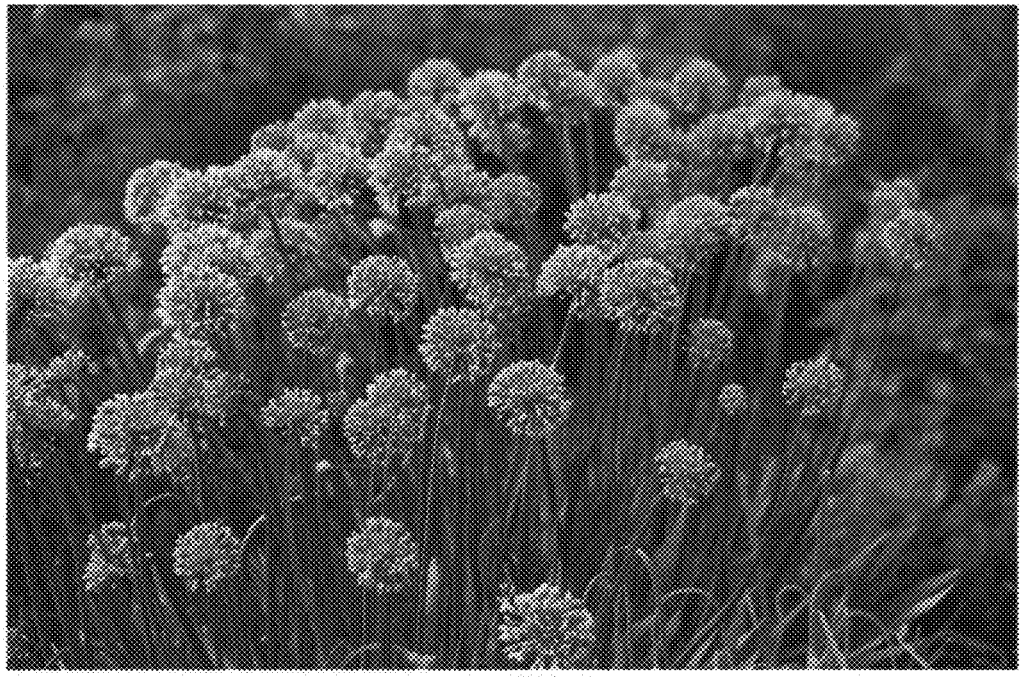

Latin name: *Allium* hybrid.
Cultivar name: 'Big Beauty'.

BACKGROUND OF THE INVENTION

The present invention relates to a new and distinct hybrid of *Allium* hybrid plant named 'Big Beauty' characterized by wide gray green foliage in combination with light purple to pink flowers, on 60 cm stems. The new *Allium* hybrid was the result of a breeding program taking place in Hebron, Ill. since 2010. 'Big Beauty' arose as a selection from seed sown from open pollination of unnamed plants of *Allium nutans*. The exact parentage of *Allium* hybrid 'Big Beauty' is unknown, however the female or seed parent is believed to be *Allium nutans*, while the male pollen parent is unknown. The selection of the new plant was due to its' wide gray green foliage in combination with light purple to pink flowers, on 60 cm stems. Asexual division propagation has been the means of reproduction. The initial cutting and division propagation has taken place at a nursery in Hebron, Ill. in 2018. The new *Allium* has shown to be stable and identical in reproduction to the parent after dividing over 1000 plants from 2018 to 2019. No plants of the new *Allium* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

The new *Allium* hybrid plant named 'Big Beauty' characterized by wide grey-green foliage in combination with light purple to pink flowers, on 60 cm stems, have been observed to be unique and stable.

Plants of the new *Allium* hybrid plant named 'Big Beauty' can be compared to *Allium* hybrid 'Summer Beauty', not patented. 1. The new plant height is typically 60 cm tall while *Allium* hybrid 'Summer Beauty' is typically 45 cm tall. 2. The new plant also has wider grey-green foliage measuring 17-20 mm wide, RHS color 137 A while *Allium* hybrid 'Summer Beauty', has green foliage RHS 137 C measuring 15 mm wide. 3. The new plant also has larger flowers RHS color 76 C, while *Allium* hybrid 'Summer Beauty', has smaller & pink flowers, RHS color not measured.

Plants of the new *Allium* hybrid plant named 'Big Beauty' can also be compared to plants of *Allium nutans* 'Nor'easter' not patented. 1. The new plant height is typically 60 cm tall while *Allium nutans* 'Nor'easter' is typically 50 cm tall. 2. The new plant also has grey-green foliage measuring 17-20 mm wide, RHS color 137 A while *Allium nutans* 'Nor'easter', has wider grey foliage measuring 20-22 mm wide.

Plants of the new *Allium* hybrid plant named 'Big Beauty' can also be compared to plants of *Allium* hybrid 'Millenium' not patented. 1. The new plant height is typically 60 cm tall while *Allium* hybrid 'Millenium' is typically 50 cm tall. 2. The new plant also has grey-green foliage measuring 17-20 mm wide, RHS color 137 A while hybrid 'Millenium', has bright green foliage measuring 15 mm wide.

DESCRIPTION OF PHOTOGRAPHS

FIG. 1. A blooming plant in July on a 2 year old plant in Hebron, Ill. USA.

Figure 2:
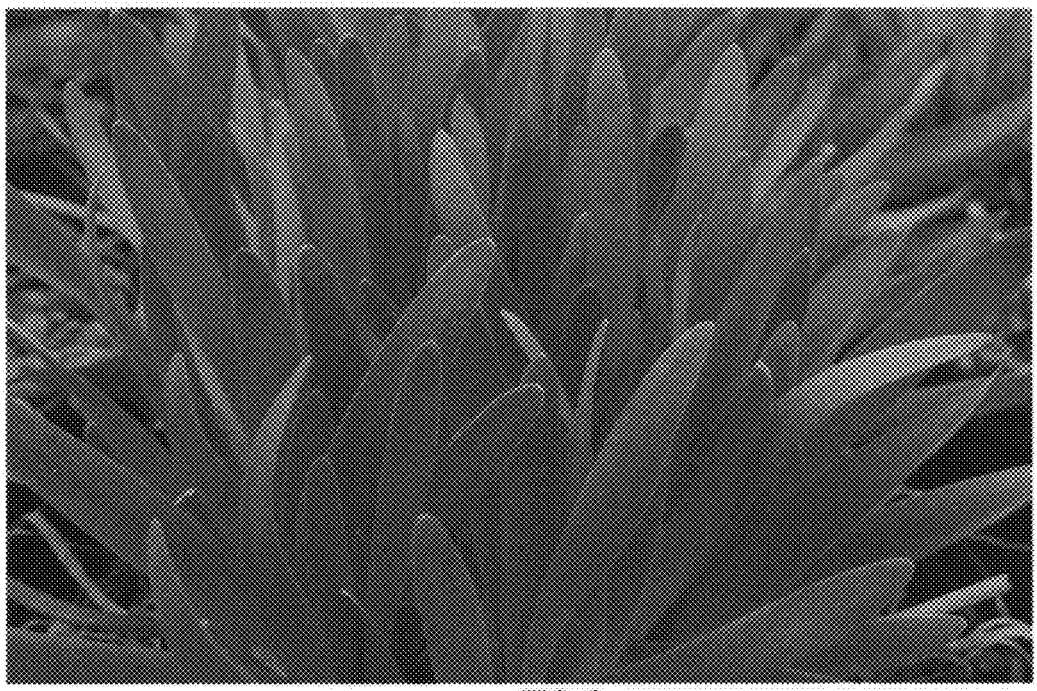

FIG. 2. Newly emerging foliage in April on a 2 year old plant in Hebron, Ill. USA.

DETAILED BOTANICAL DESCRIPTION

In the following description, color references are made to The Royal Horticultural Society Colour Chart (2001). Plants used for the description were grown in a three gallon container for two years at a nursery in Hebron, Ill. Measurements and numerical values represent averages of typical plants.

Botanical classification: *Allium* hybrid cultivar 'Big Beauty'.

Parentage: Female/seed parent. An open pollinated *Allium nutans*, male parent an unknown *Allium*.

Propagation: Vegetative division.

Plant description:

*Type.*—Herbaceous perennial. The overall habit of the new *Allium* hybrid is a basal tuft of grey-green linear foliage arising from bulbous roots, with terminal light purple to pink flower clusters in July.

*Hardiness.*—USDA zones 3-8.

*Plant height.*—60 cm.

*Plant width.*—60 cm.

Stem description:

*Stem shape.*—Round with ridges, solid.

*Stem size.*—Diameter — up to 10 mm at the widest by 7 mm at the thinnest.

*Stem length.*—50 cm.

*Internodes.*—None.

*Stem coloration.*—Stem color 137 A, lighter at the base.

*Stem texture.*—Ridged, smooth, and glabrous.

*Roots.*—Fibrous below the bulb, color 156 D.

*Bulb.*—Size — 35 mm wide at the base, 26 mm wide at the top where the foliage begins, 35 mm in length, color: 155 D.

Foliage description:

*Shape.*—Linear.

*Arrangement.*—Basal, alternate.

*Leaf blade size.*—Length: up to 33 cm, Width: 17-20 mm.

*Margins.*—Entire.

*Petiole.*—None.

*Leaf apex.*—Acute.

*Leaf base.*—Attenuate.

*Leaf quantity.*—An average of 15 per bulb.

*Texture.*—Upper and lower surfaces: smooth, glabrous.

*Adaxial and abaxial leaf color description.*—137 A.

*Venation pattern.*—Parallel.

*Venation color.*—Upper 137 A, lower 137 A.

Flower description:

*Inflorescence type.*—Umbel, round, held on a leafless stalk.

*Umbel size.*—Length: 65 mm tall, width: 75 mm.

*Peduncle size and color.*—Length: 25 mm, diameter: 1 mm, color — 146 C.

*Peduncle texture.*—Smooth, glabrous.

*Pedicel size and color.*—Length: 25 mm, width 1 mm, color — 146 C.

*Flower bud.*—Size: length: 15 mm, diameter: 40-45 mm.

*Flower bud surface.*—Smooth, glabrous.

*Flower bud shape.*—Ovoid, tubular, constricted at the base.

*Flower bud color.*—Between 85 A and 76 A.

*Corolla description.*—3 petals unfused, constricted at the base.

*Petal apex.*—Entire, acute.

*Petal base.*—Unfused.

*Petal margin.*—Entire.

*Petal texture.*—Outer surface: smooth, inside surface: smooth.

*Petal color: outer surface.*—Is color 76 B, inside surface — color is 76 A and B.

*Calyx shape.*—Stellate.

*Calyx size.*—Length: 7 mm, Width: 3 mm.

*Calyx color.*—76 B.

*Sepal quantity and arrangement.*—3, unfused.

*Sepal size.*—Length: 7 mm, diameter: 3 mm at base coming to a point.

*Sepal shape.*—Lanceolate, apex: acute, base: cuneate, margin: entire.

*Sepal texture.*—Upper and lower surfaces: smooth, glabrous.

*Sepal color.*—Adaxial color 76 B, Abaxial color 76 B.

*Flower type and shape.*—Bowl, comprised of 3 sepals and 3 petals.

*Flower color.*—76 B outside, 76 A & B inside.

*Flower size.*—Length: 10 mm, width: 10 mm.

*Flower number.*—185 per umbel, 5000 per plant with up to 50 flowering stems.

*Bloom period and duration.*—3-4 weeks the beginning of July in Hebron, Ill.

*Flower longevity and duration on the plant.*—Approximately 3 weeks.

*Flower longevity and duration cut.*—Not measured.

*Scent.*—None.

Reproductive organs:

*Stamen.*—Quantity: 6, length: 10 mm, diameter: 1 mm at the base getting thinner toward the tip.

*Anther.*—Quantity: 6, length: 2 mm, diameter: 1 mm.

*Anther shape.*—Oval, color between N187 B & C.

*Filament.*—76 B at tip near anther, cream colored at the base.

*Pollen.*—Sparse, color: not measurable RHS color not measured.

*Pistil.*—Number: 1, length: 4 mm, width: 1 mm, color — 76 B.

*Stigma shape.*—Conical, color — 76 B.

*Style.*—Number: 1, length: 4 mm, width 1 mm.

*Ovaries.*—Made of 3 carpels, length: 2-3 mm, width: 1-2 mm.

*Fruit.*—Capsule more or less round, 5 mm long, 3-4 mm wide, glabrous, color brown-black 202 A.

Disease resistance: Resistance to diseases common to *Allium* has not been observed on plants grown under nursery conditions.

I claim:

1. A new, distinct *Allium* hybrid plant as shown and described, characterized by wide gray green foliage in combination with light purple to pink flowers, on 60 cm stems.

* * * * *